United States Patent
Vesma

(10) Patent No.: US 9,562,845 B2
(45) Date of Patent: Feb. 7, 2017

(54) TECHNIQUE FOR TEMPERATURE CONTROLLING POLARIMETER SAMPLE CELLS

(71) Applicant: XYLEM IP UK S. à. r. l., Senningerberg (LU)

(72) Inventor: Valdis R. Vesma, Wadhurst (GB)

(73) Assignee: Xylem IP UK S. A R. L., Senningerber (LU)

( * ) Notice: Subject to any disclaimer, the term of this patent is extended or adjusted under 35 U.S.C. 154(b) by 0 days.

(21) Appl. No.: 15/045,712

(22) Filed: Feb. 17, 2016

(65) Prior Publication Data

US 2016/0245740 A1 Aug. 25, 2016

Related U.S. Application Data

(60) Provisional application No. 62/117,296, filed on Feb. 17, 2015.

(51) Int. Cl.
*G01B 11/16* (2006.01)
*G01N 21/03* (2006.01)
*G01N 21/21* (2006.01)

(52) U.S. Cl.
CPC .......... *G01N 21/0332* (2013.01); *G01N 21/21* (2013.01); *G01N 2201/061* (2013.01); *G01N 2201/062* (2013.01)

(58) Field of Classification Search
CPC .. G01N 35/0098; G01N 21/6428; G01N 1/31; G01N 35/0092; G01N 35/04; G01N 35/1002; G01N 35/1011; G01N 2035/00752; G01N 2201/062; G01N 35/00732; G01N 2035/0465; G01N 1/38; G01N 2021/6484
See application file for complete search history.

(56) References Cited

U.S. PATENT DOCUMENTS 3,817,629 A 6/1974 Witte
4,066,365 A 1/1978 Staunton
(Continued)

FOREIGN PATENT DOCUMENTS

CN 101424616 12/2007
DE 3516529 11/1986
(Continued)

OTHER PUBLICATIONS

International Search Report and Written Opinion issued by the USPTO on Apr. 29, 2016 in counterpart international patent application No. PCT/US2016/018228 (7 pages).

*Primary Examiner* — Michael P Stafira
(74) *Attorney, Agent, or Firm* — Ware, Fressola, Maguire & Barber LLP

(57) ABSTRACT

Apparatus features a sample tube adapter made of conductive material, having a first part to contain and touch a sample tube having a sample therein, and a second part to provide a thermal path for heat transfer to/from the sample tube and a thermal assembly for performing a sample analysis; and sample support rails to receive the sample tube adapter to provide physical support for the sample tube, orient the sample tube adapter in relation to the thermal assembly so there is contact between the sample tube adapter and the thermal assembly to provide the thermal path for heat transfer to/from the sample tube and the thermal assembly, and align the sample tube adapter in relation to a light source so there is a registration between the sample tube and a light beam provided by the light source, all for performing the sample analysis.

15 Claims, 6 Drawing Sheets

(56) References Cited

U.S. PATENT DOCUMENTS

| | | | |
|---|---|---|---|
| 4,180,739 A | 12/1979 | Abu-Shumays | |
| 4,547,069 A | 10/1985 | Lersmacher et al. | |
| 4,699,514 A | 10/1987 | Schmidt et al. | |
| 4,822,169 A | 4/1989 | Distl et al. | |
| 5,033,852 A | 7/1991 | Zaglio | |
| 5,146,283 A | 9/1992 | Parnoff et al. | |
| 5,436,457 A | 7/1995 | Tomita | |
| 5,509,733 A * | 4/1996 | Danley | G01N 25/4826 374/11 |
| 5,607,643 A | 3/1997 | Xiaoming et al. | |
| 5,924,290 A | 7/1999 | Yoshino | |
| 6,046,804 A | 4/2000 | Kawamura et al. | |
| 6,717,665 B2 | 4/2004 | Wagner et al. | |
| 6,901,095 B2 | 5/2005 | Tsunetomo et al. | |
| 6,920,399 B2 | 7/2005 | Priev et al. | |
| 7,075,652 B1 | 7/2006 | Sarvazyan et al. | |
| 7,092,154 B2 | 8/2006 | Yasuda et al. | |
| 7,108,970 B2 | 9/2006 | Levinson | |
| 7,443,503 B2 | 10/2008 | Kubo et al. | |
| 7,468,788 B2 | 12/2008 | Gibbs et al. | |
| 7,520,683 B2 | 4/2009 | Takai et al. | |
| 7,884,932 B2 | 2/2011 | Wachernig et al. | |
| 8,014,961 B2 | 9/2011 | Bass et al. | |
| 8,134,707 B2 | 3/2012 | Bornhop et al. | |
| 8,663,575 B2 | 3/2014 | Maurer et al. | |
| 8,908,179 B2 | 12/2014 | Ostermeyer | |
| 2003/0174323 A1 | 9/2003 | Wagner et al. | |
| 2005/0085416 A1 | 4/2005 | Svanborg et al. | |
| 2005/0117152 A1 | 6/2005 | Barnikol et al. | |
| 2011/0012513 A1 | 1/2011 | Yilmaz | |
| 2013/0319078 A1* | 12/2013 | Mahoney | G01N 33/28 73/19.11 |

FOREIGN PATENT DOCUMENTS

| | | |
|---|---|---|
| EP | 1174183 | 1/2002 |
| GB | 2360830 | 10/2001 |
| JP | 2003179296 | 6/2003 |

\* cited by examiner

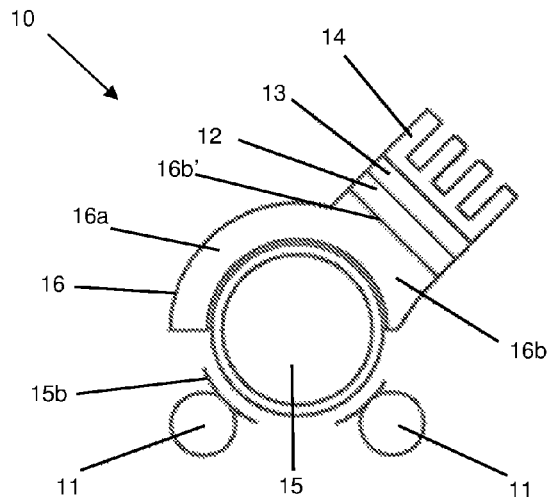
Figure 2A
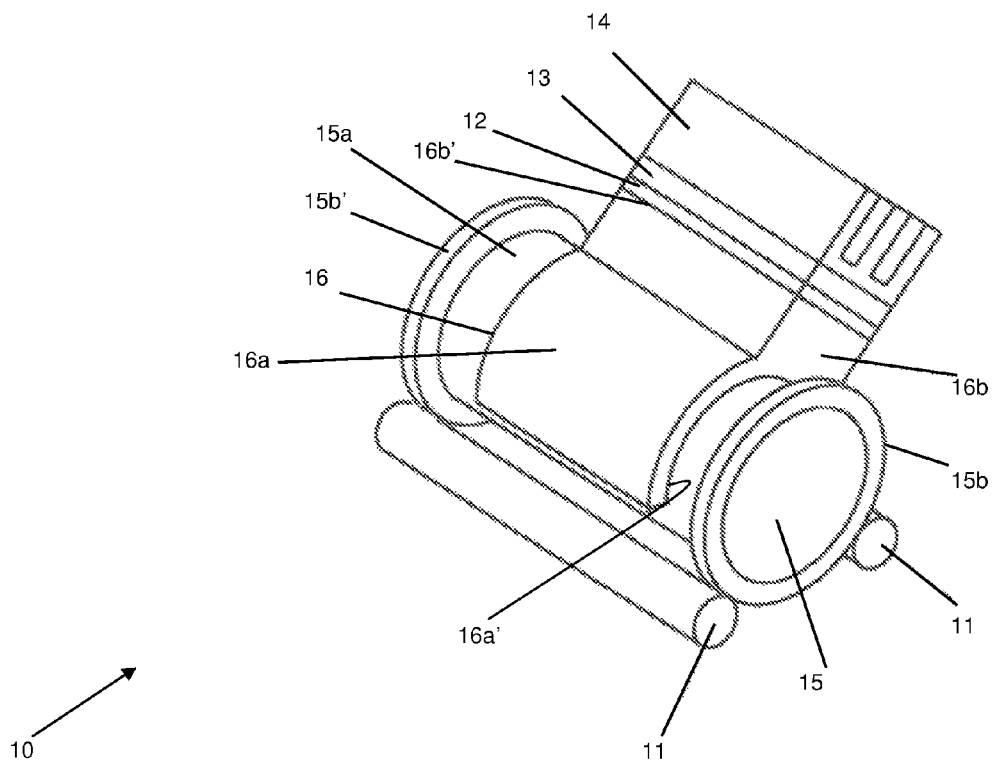
Figure 2B
Figure 2

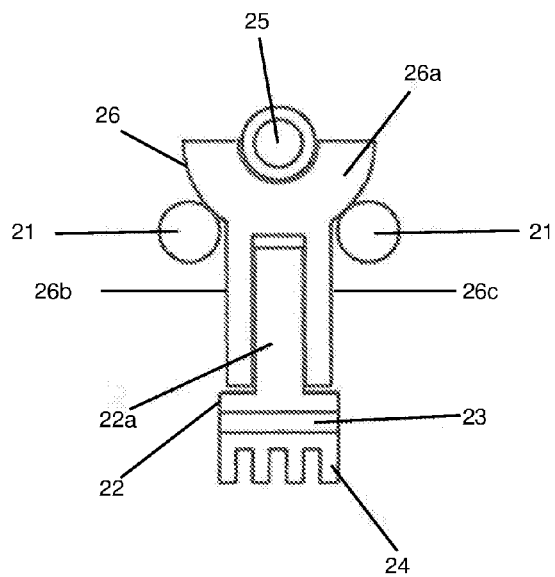
Figure 3A
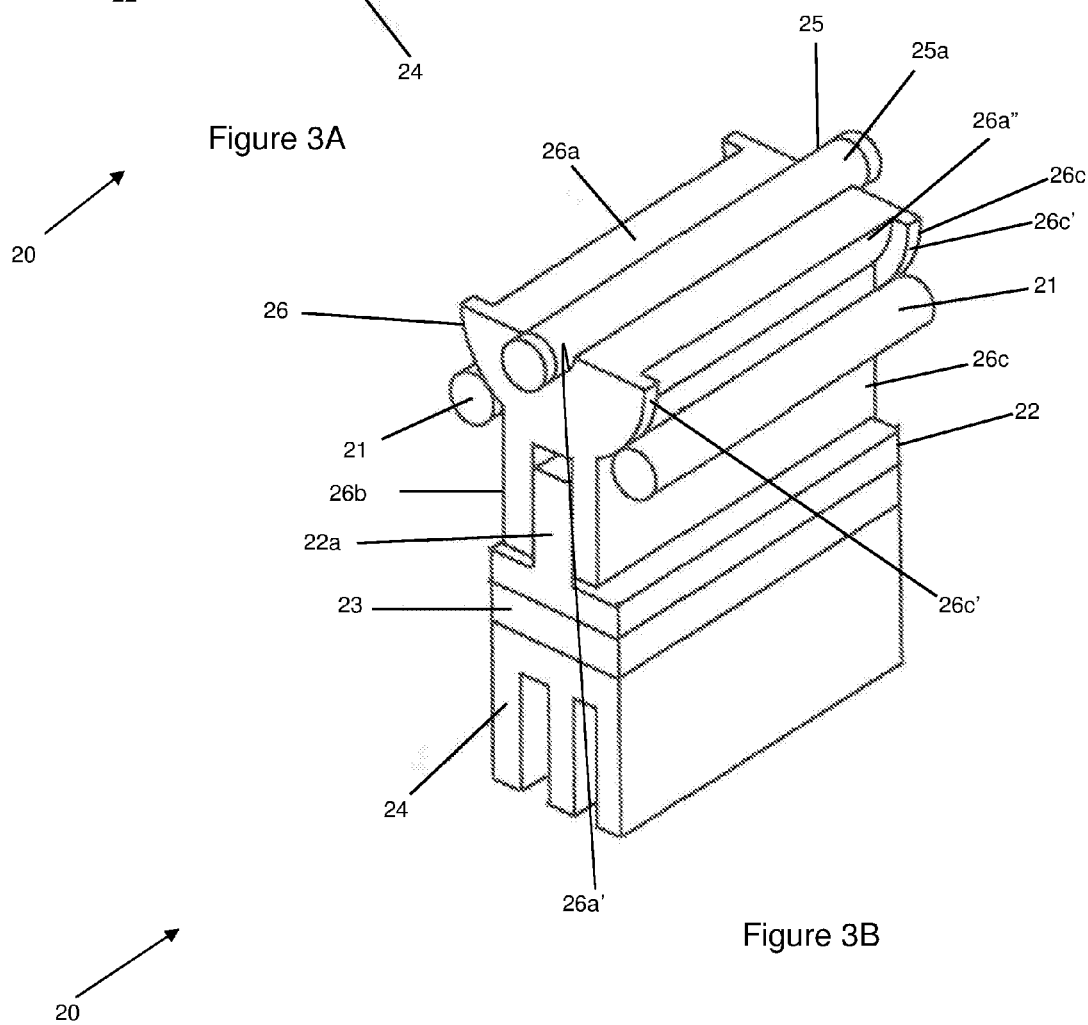
Figure 3B
Figure 3

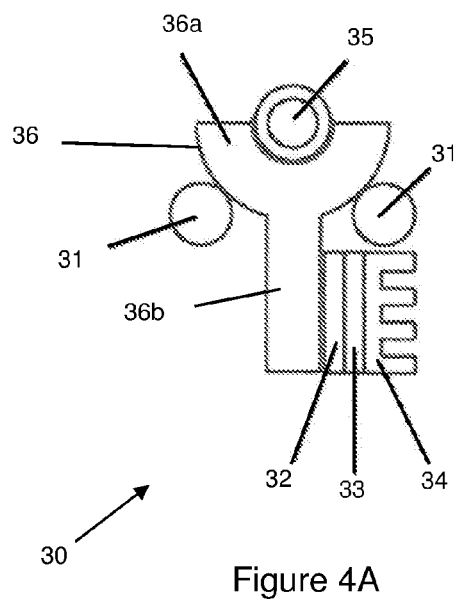
Figure 4A
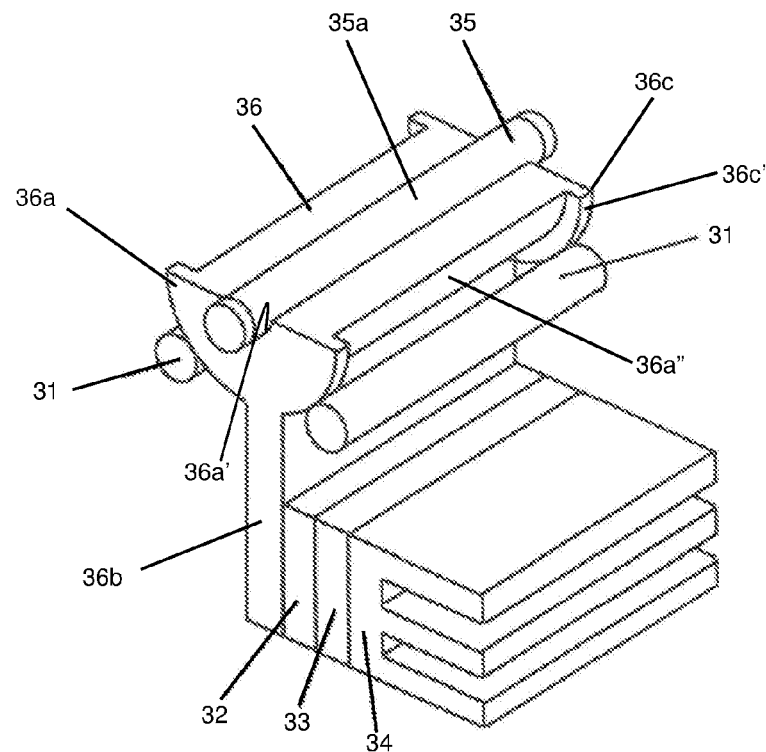
Figure 4B
Figure 4

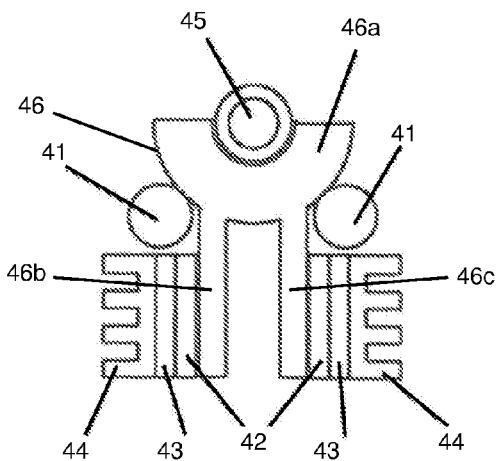
Figure 5A
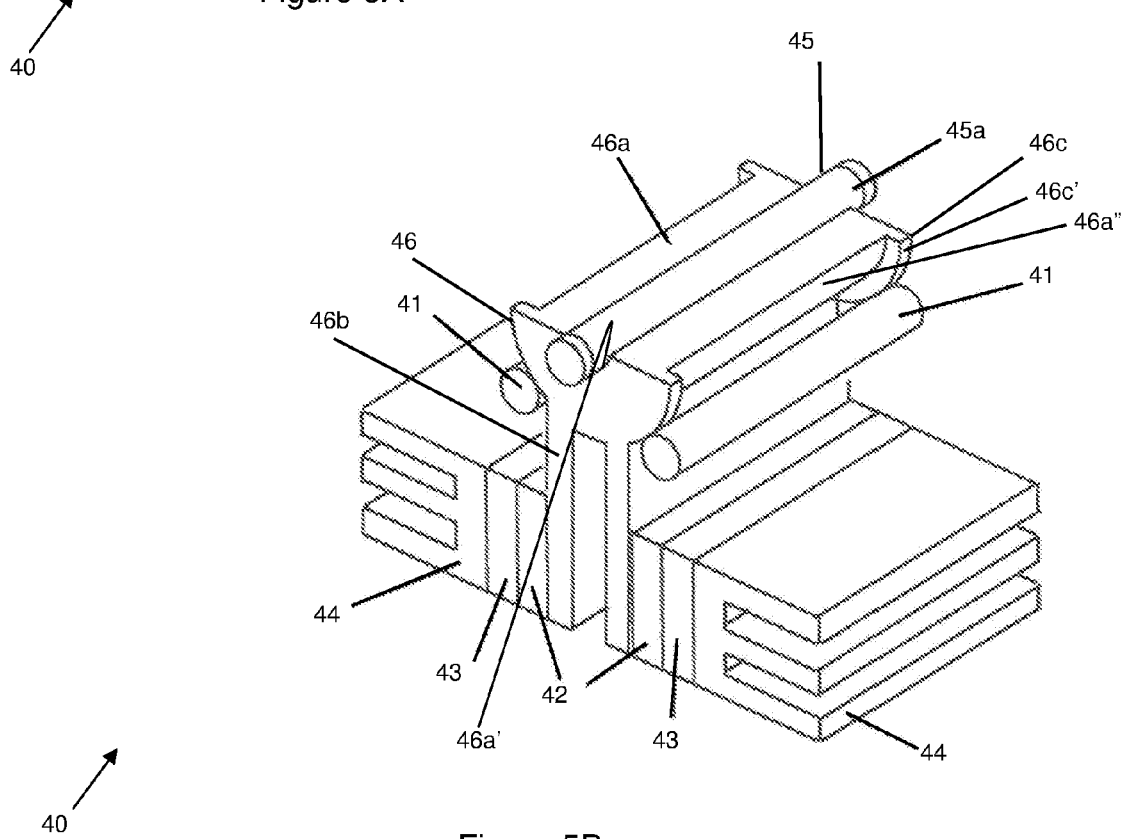
Figure 5B
Figure 5

TECHNIQUE FOR TEMPERATURE CONTROLLING POLARIMETER SAMPLE CELLS

CROSS REFERENCE TO RELATED APPLICATION

This application claims benefit to U.S. provisional application No. 62/117,296, filed 17 Feb. 2015, which is hereby incorporated by reference in its entirety.

BACKGROUND OF THE INVENTION

1. Field of the Invention

The present invention relates to a technique for implementation of a Peltier controlled sample in a polarimeter.

2. Brief Description of Related Art

As a person skilled in the art would appreciate, a polarimeter is an instrument known in the art for measuring optical activity exhibited by an optically active substance. In operation, the plane of polarization of a linearly polarized light beam may be rotated when passing through the optically active substance, and the rotation may be determined by the specific substance, the concentration of that substance and the optical path length of the light through the substance contained in the sample cell, whereby the concentration of the specific substance can be calculated by the measured rotation. The optical rotation may also be affected by the temperature of the substance contained in the sample cell, and thus it may be desirable, and in many cases required by governing regulations, that the temperature of the sample substance be controlled to be at a set point for precise measurement.

With this backdrop, and by way of example, some known techniques for implementation of a Peltier controlled sample using such a polarimeter may include the following technique:

Known techniques for implementation of a Peltier controlled sample in a polarimeter may include using a sample cell that is a cylindrical tube so as to minimize the amount of the sample substance that is in the cell but not in the light path, referred to as "dead volume". Flanges are provided at opposite ends of the sample cell, each with a beam aperture therein for allowing the polarized light beam to pass therethrough. The flanges are usually standard in size for properly positioning the sample cell in the light path when the pair of flanges sit on the cell holder constituted by a parallel rails. The flanges may be removable from the sample cell to facilitate cleaning of the sample cell. The temperature control of the sample substance is realized by circulating water in a water jacket around the external surface of the sample cell containing the sample substance. The water jacket is formed by an outer tube communicated with a water tube connected to a water source at a predetermined temperature. However, as a person skilled in the art may appreciate such a water temperature control system is complicated in structure, comprising a water jacket and cooling tubes. Furthermore, as a person skilled in the art may also appreciate it is inconvenient to connect and disconnect the tubing when cleaning the cell and changing the sample, and it also takes long time to change the temperature set point.

Other known techniques for implementation of a Peltier controlled sample in a polarimeter may include thermoelectric temperature control techniques, such as thermo electric coolers (TEC). For example, the temperature of one side of a TEC device, which is usually a flat plate in shape, is controllable by an electric current. Heat can be made to flow through the device in either direction as required. A TEC element with a heat sink is provided to be thermally conductive with a rectangular cell holder accommodating a rectangular sample cell. A polarized light beam passes through the sample cell via the apertures provided on the cell holder. The solid TEC element appears to eliminate the complication and inconvenience of the water tubing required in the conventional cylindrical cell samples. Furthermore, the temperature of the cell holder and therefore the sample cell can be easily and quickly controlled at a set point. However, the rectangular sample cell assumes a high dead volume and requires a larger sample volume to fill. This is costly when the measured substance is precious. Another problem with such a rectangular structural design appears to be that the cell holder cannot work with conventional standard cylindrical sample cells which are commonly used in the industry. In addition this design was not able to control temperature within the limits required by relevant governing regulations.

Still other known techniques for implementation of a Peltier controlled sample in a polarimeter may include using a combination of a slanted flat base plate and a single horizontal rail, e.g., where the slanted flat based plate is made of heat conductive material for transferring heat between a thermal electric conductor (TEC) and a material inside a sample cell, where the flat slanted based plate is biased to urge the sample cell against the single horizontal rail, and the combination positions the sample cell at a predetermined position such that a polarized light beam longitudinally passes through the sample cell.

Still other known techniques for implementation of a Peltier controlled sample in a polarimeter may include using a combination of a slanted flat base plate and a stopper or side wall to position a sample cell at a predetermined position such that a polarized light beam longitudinally passes through the sample cell.

Still other known techniques for implementation of a Peltier controlled sample in a polarimeter may include using a combination of parallel rails and a base plate having a dovetail connection to a base plate that is mounted on top of a sample cell, where the base plate is not secured relative to a light beam path and has no position function into relation to same.

Other techniques for implementation of a Peltier controlled sample using such a polarimeter are also known in the art and not set forth therein, e.g., including those set forth in prior art provided to the Patent Office during the prosecution of this patent application.

SUMMARY OF THE INVENTION

By way of example, the present invention provides a new and unique technique for implementation of a Peltier controlled sample in a polarimeter.

According to some embodiments, and by way of example, the present invention may include, or take the form of, apparatus configured to perform a sample analysis of a sample contained in a sample tube, featuring a combination of a sample tube adapter and sample support rails.

The sample tube adapter may be made of conductive material, and configured with a first part to at least partially contain and touch a sample tube having a sample therein, and configured with a second part to provide a thermal path for heat transfer to and from the sample tube and a thermal assembly for performing a sample analysis.

The sample support rails may be configured to
  receive the sample tube adapter to provide physical support for the sample tube for performing the sample analysis,
  orient the sample tube adapter in relation to the thermal assembly so there is contact between the second part of the sample tube adapter and some part of the thermal assembly in order to provide the thermal path for heat transfer to and from the sample tube and the thermal assembly for performing the sample analysis, and
  align the sample tube adapter in relation to a light source so there is a registration between the sample tube and a light beam provided by the light source for performing the sample analysis.

The present invention may include one or more of the following features:

The first part of the sample tube adaptor may include an inner curved surface to rest on, and make contact with, an outer curved surface of the sample tube having the sample therein.

The second part of the sample tube adaptor may include a flat surface to make contact with a temperature control plate of the thermal assembly.

The sample tube adaptor may include two end raised flange portions configured to rest on, and be supported by, the sample support rails.

The inner curved surface may be U-shaped, e.g., to contain and envelope the sample tube.

The sample support rails may be configured to extend in parallel with one another, e.g., including extending in parallel with the longitudinal axis of the sample tube.

The sample tube adaptor may include a curved exterior surface configured to rest on, and make contact with, an outer curved surface of the sample tube having the sample therein. The curved exterior surface may be semicylindrical, e.g., substantially having the shape of a longitudinal half of a cylinder The second part of the sample tube adaptor may include two blades extending downwardly that straddle a vertical blade extending upwardly of a temperature control plate of the thermal assembly to provide the thermal path for heat transfer to and from the sample tube and the thermal assembly for performing the sample analysis.

The second part of the sample tube adaptor may include a blade extending downwardly having a blade surface that abuts against a temperature control plate of the thermal assembly to provide the thermal path for heat transfer to and from the sample tube and the thermal assembly for performing the sample analysis.

The second part of the sample tube adaptor may include two blades extending downwardly, each blade having a corresponding blade surface that respectively abuts against a corresponding temperature control plate of the thermal assembly to provide the thermal path for heat transfer to and from the sample tube and the thermal assembly for performing the sample analysis.

The apparatus may include the thermal assembly, e.g., having a combination of a temperature control plate, a Peltier device and a heatsink.

The apparatus may include the light source for providing the light beam, e.g., including where the light source is a laser and the light beam is a laser beam. The light source may also include either an incandescent lamp for providing an incandescent light beam, or a light emitting diode (LED) for providing an LED light beam.

The apparatus may include the thermal assembly and the light source; and may also include an instrument chassis configured to fixedly mount the sample support rails in relation to the thermal assembly and the light source, so that when the sample support rails receive the sample tube adapter, the sample support rails orient the sample tube adapter in relation to the thermal assembly so there is contact between the second part of the sample tube adapter and the part of the thermal assembly in order to provide the thermal path for heat transfer to and from the sample tube and the thermal assembly for performing the sample analysis, and align the sample tube adapter in relation to the light source so there is a registration between the sample tube and a light beam provided by the light source for performing the sample analysis.

The apparatus may include a detector/analyzer configured to receive the light beam passing through the sample tube and perform the sample analysis.

BRIEF DESCRIPTION OF THE DRAWING

The drawing includes the following Figures, which are not necessarily drawn to scale:

FIG. 1A is a diagram showing a view of a polarimeter along its longitudinal axis, and where FIG. 1B is a diagram showing a perspective view of the polarimeter shown in FIG. 1A, according to some embodiments of the present invention.

FIG. 2 includes FIGS. 2A and 2B, where FIG. 2A is a diagram showing a view of a polarimeter along its longitudinal axis, and where FIG. 2B is a diagram showing a perspective view of the polarimeter shown in FIG. 2A, according to some embodiments of the present invention.

FIG. 3 includes FIGS. 3A and 3B, where FIG. 3A is a diagram showing a view of a polarimeter along its longitudinal axis, and where FIG. 3B is a diagram showing a perspective view of the polarimeter shown in FIG. 3A, according to some embodiments of the present invention.

FIG. 4 includes FIGS. 4A and 4B, where FIG. 4A is a diagram showing a view of a polarimeter along its longitudinal axis, and where FIG. 4B is a diagram showing a perspective view of the polarimeter shown in FIG. 4A, according to some embodiments of the present invention.

FIG. 5 includes FIGS. 5A and 5B, where FIG. 5A is a diagram showing a view of a polarimeter along its longitudinal axis, and where FIG. 5B is a diagram showing a perspective view of the polarimeter shown in FIG. 5A, according to some embodiments of the present invention.

DETAILED DESCRIPTION OF THE INVENTION

Figure 1:
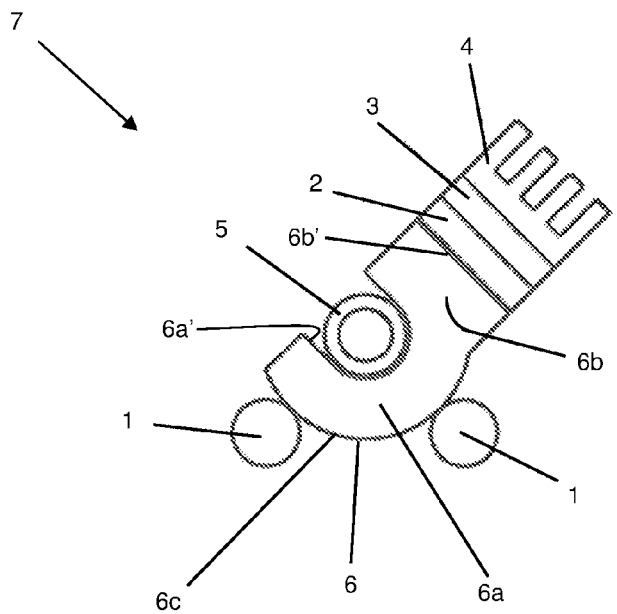
FIG. 1 includes FIGS. 1A and 1B, where
Figure 1:
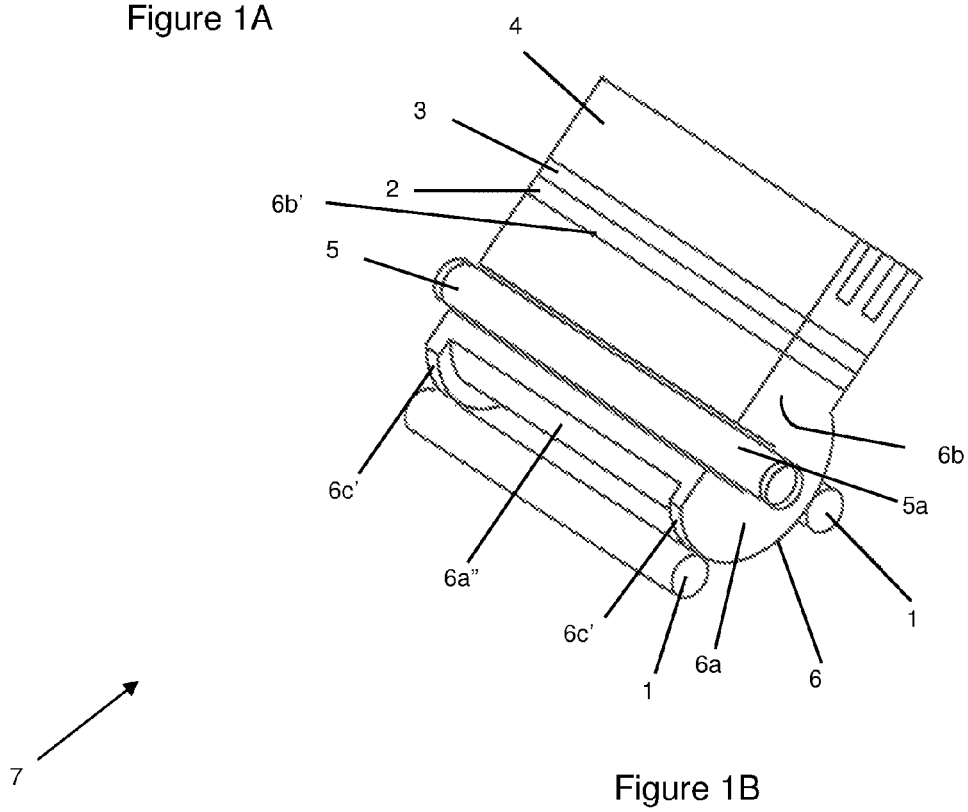

1. Three Key Elements of the Overall System

In summary, the following is a technical/detailed description for the implementation of Peltier controlled sample in a polarimeter, according to some embodiments of the present invention. By way of example, and consistent with that shown in the drawing, including FIGS. 1-6, the overall system, equipment or apparatus may be configured to provide the following three key elements for sample analysis:
  a. Physical support for the sample tube;
  b. Registration between the sample tube and a light beam; and
  c. A thermal path for heat transfer to or from the sample tube.

The structure and function of the basic components/parts of the present invention for implementing these three key elements for sample analysis is described in further detail below.

2. The Components/Parts

By way of example, and consistent with that shown in FIGS. 1-6, and also according to some embodiments of the present invention, the polarimeter generally indicated as (7, 10, 20, 30, 40) may include the following component or parts:
- a. Sample Support Rails (1, 11, 21, 31, 41),
- b. Temperature Controlled Plate (2, 12, 22, 32, 42),
- c. Peltier Devices (3, 13, 23, 33, 43),
- d. Heatsink (4, 14, 24, 34, 44),
- e. Sample Tube (5, 15, 25, 35, 45), and
- f. Sample Tube Adaptor (6, 16, 26, 36, 46).

Figure 6:
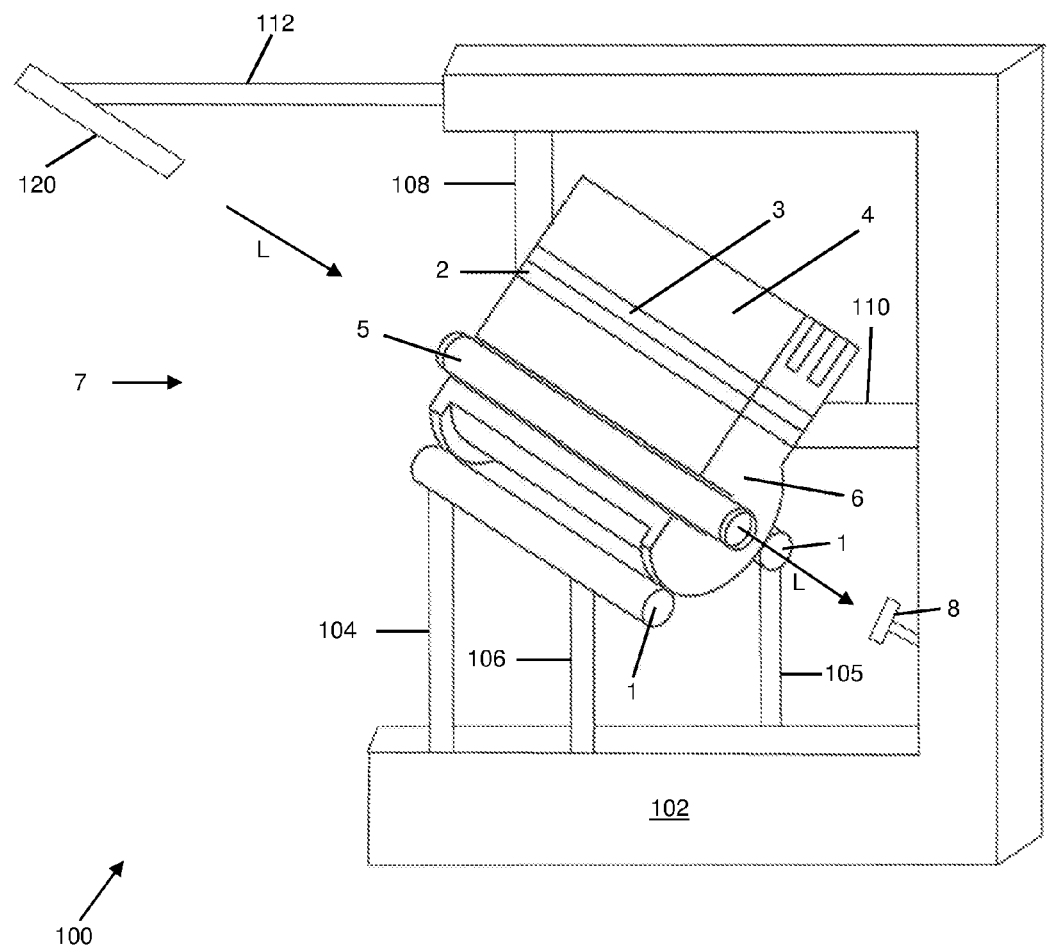
FIG. 6 is a diagram of the polarimeter shown in FIG. 1B arranged in relation to an instrument chassis, according to some embodiments of the present invention.

By way of example, FIG. 6 shows the overall system, equipment or apparatus generally indicated as (100) having the polarimeter (7) arranged in relation to a frame-like structure or instrument chassis (102) for performing the sample analysis, e.g., consistent with that described below.

3. Functional Description of Component/Parts

The basic function of component/part are described as follows:
- a. The sample support rails (1, 11, 21, 31, 41) provides two of the three key elements for both standard polarimeter sample tubes and the sample tube adaptor (6, 16, 26, 36, 46), including:
  - 1st key element: Physical support for the sample tube (5, 15, 25, 35, 45), and
  - 2nd key element: Registration between the sample tube (5, 15, 25, 35, 45) and a light beam (not shown).
- b. The temperature controlled plate (2, 12, 22, 32, 42) touches the sample tube adaptor (6, 16, 26, 36, 46) thereby providing:
  - the 3rd key element, i.e., a thermal path for heat transfer to or from the sample tube (5, 15, 25, 35, 45).
- c. The Peltier devices (3, 13, 23, 33, 43) provide a method of pumping heat to or from the temperature controlled plate (2, 12, 22, 32, 42).
- d. The heatsink (4, 14, 24, 34, 44) provides a method of absorbing or dissipating heat pumped via Peltier devices (3, 13, 23, 33, 43).
- e. The sample tube (5, 15, 25, 35, 45) holds the sample to be analysed. f. The sample tube adaptor (6, 16, 26, 36, 46) is made of thermally conductive material and combines the three key elements (See 1a, 1b and 1c above) to provide the required physical and thermal environment for sample analysis. The sample tube adaptor (6, 16, 26, 36, 46) can be made in different sizes to cater for sample tubes of any length, diameter, shape or form. The 'cotton-reel' design permits the sample tube adaptor (6, 16, 26, 36, 46) to rest on the sample support rails (1, 11, 21, 31, 41) with minimum contact area thereby limiting heat leakage to the sample support rails (1, 11, 21, 31, 41).
- g. According to some embodiments of the present invention, standard polarimeter tubes may be used without thermal control.

4. Structural Description of Component/Parts

The basic structure of the component/part is as follows:
- a. The temperature controlled plate (2, 12, 22, 32, 42), Peltier devices (3, 13, 23, 33, 43) and heatsink (4, 14, 24, 34, 44) are structurally combined to form one assembly (AKA a so-called "thermal assembly") and is supported by the instrument chassis, e.g., consistent with that shown in FIGS. 1-5.
- b. The sample tube adaptor (6, 16, 26, 36, 46) physically rests on the sample support rails (1, 11, 21, 31, 41), e.g., consistent with that set forth as follows.
  - i. For the embodiments shown in FIGS. 1 and 2, the position of the thermal assembly may be laterally adjusted to ensure correct mating between the temperature controlled plate (2, 12) and sample tube adaptor (6, 16).
  - ii. For the embodiments shown in FIGS. 3, 4 and 5, correct mating between the temperature controlled plate (22, 32, 42) and sample tube adaptor (26, 36, 46) would typically require the thermal assembly to be pre-positioned during product assembly.
- c. The sample tube (5, 15, 25, 35, 45) physically rests on the sample tube adaptor (6, 16, 26, 36, 46), e.g., consistent with that shown in FIGS. 1-5.
- d. The sample tube (5, 15, 25, 35, 45) may be combined with or designed as part of the sample tube adaptor (6, 16, 26, 36, 46) forming one specific assembly, e.g., consistent with that shown in FIGS. 1-5.

FIGS. 1 and 2

FIG. 1 shows apparatus generally indicated as 7 for implementing some embodiments of the present invention. By way of example, in FIG. 1 shows the sample tube adaptor (6) has a U-shaped part (6a) and a portion (6b) having a flat surface (6b′) for contacting the temperature controlled plate (2). The U-shaped part (6a) has an inner U-shaped surface (6a′) and an outer U-shaped surface (6a″) configured between two raised flange portions (6c), as labelled in FIG. 1A. Each raised flange portions (6c) has a respective raised flange portion surfaces (6c′), as labelled in FIG. 1B. The inner U-shaped surface (6a′) rests on an outer sample tube surface (5a) of the sample tube (5). The two raised flange portions (6c) rest on and are supported by the sample support rails (1), e.g., consistent with that shown in FIG. 1. Contact between the sample tube adaptor (6) and the temperature controlled plate (2) is maintained by a proximity/friction fit.

FIG. 2 shows apparatus generally indicated as 10 for implementing some embodiments of the present invention. By way of example, in FIG. 2, the sample tube adaptor (16) has a U-shaped part (16a) and a portion (16b) having a flat surface (16b′) for contacting the temperature controlled plate (22). The U-shaped part (16a) has an inner U-shaped surface (16a′) that rests on an outer cylindrical surface (15a) of the sample tube (15) between two outer raised flange portions (15b). The two outer raised flange portions (15b) each have a respective outer raised flange portion surfaces (15b′), as labelled in FIG. 2B, that respectively rest on and are supported by the sample support rails (1), e.g., consistent with that shown in FIG. 2. Contact between the sample tube adaptor (16) and the temperature controlled plate (12) is maintained by a proximity/friction fit.

FIGS. 1 and 2 show embodiments that may be considered preferred implementations, which have the following advantages:

i. The thermal assembly (see section 4(a)) is configured above the level of the sample which provides a degree of protection from sample leakage;
ii. The position of the thermal assembly (see 5(a)) is adjustable in relation to the sample tube adaptor (6, 16) thereby providing best possible thermal contact;
iii. Sample leakage collects at the bottom of the instrument chamber and may be easily removed;
iv. The embodiments are simple to engineer and maintain; and
v. The "over saddle" arrangement in FIG. 2 permits the thermal control of tubes up to the maximum possible diameter.

By way example, and for the purpose of the discussion herein, the term "U-shaped" is understood to mean having the shape substantially like the letter "U".

FIG. 3

FIG. 3 shows apparatus generally indicated as 20 for implementing some embodiments of the present invention. By way of example, in FIG. 3, the sample tube adaptor (26) has a U-shaped part (26a) and two blades (26b, 26c) extending downwards that straddle a vertical blade (22a) on the temperature controlled plate (22). The vertical blade (22a) on the temperature controlled plate (22) is configured and dimensioned to fit within the two blades (26b, 26c) of the U-shaped part (26a). The U-shaped part (26a) has an inner U-shaped surface (26a') and an outer U-shaped surface (26a") configured between two raised flange portions (26c), as labelled in FIG. 3B. Each raised flange portions (26c) has a respective raised flange portion surfaces (26c'), as labelled in FIG. 3B. The inner U-shaped surface (26a') rests on an outer sample tube surface (25a) of the sample tube (25). The two raised flange portions (26c) rest on and are supported by the sample support rails (21), e.g., consistent with that shown in FIG. 3. Contact between the downwardly extending two blades (26b, 26c) of the sample tube adaptor (26) and the vertical blade (22a) of the temperature controlled plate (22) allow for heat transfer, and the contact therebetween is maintained by a proximity/friction fit. The same level of versatility of the sample tube adaptor (26) applies (as set forth in section 3(f) above).

FIG. 4

FIG. 4 shows apparatus generally indicated as 30 for implementing some embodiments of the present invention. By way of example, in FIG. 4, the sample tube adaptor (36) has a U-shaped part (36a) connected to one blade (36b) extending downwards that abuts the temperature controlled plate (32). Contact between the sample tube adaptor (36) and the temperature controlled plate (32) may be maintained, e.g., by a spring or magnetic force. The same level of versatility of the sample tube adaptor (36) applies (as set forth in section 3(f) above).

Similar to that shown in FIG. 3, the embodiment in FIG. 4 includes the U-shaped part (36a) having an inner U-shaped surface (36a') and an outer U-shaped surface (36a") configured between two raised flange portions (36c), as labelled in FIG. 4B. Each raised flange portions (36c) has a respective raised flange portion surfaces (36c'), as labelled in FIG. 4B. The inner U-shaped surface (36a') rests on an outer sample tube surface (35a) of the sample tube (35). The two raised flange portions (36c) rest on and are supported by the sample support rails (31), e.g., consistent with that shown in FIG. 4.

FIG. 5

FIG. 5 shows apparatus generally indicated as 40 for implementing some embodiments of the present invention. By way of example, in FIG. 5, the sample tube adaptor (46) has a U-shaped part (46a) connected to two blades (46b, 46c) extending downwards that are placed between two temperature controlled plates (42). Contact between the sample tube adaptor (46) and the temperature controlled plates (42) is maintained by a proximity/friction fit. The same level of versatility of the sample tube adaptor (46) applies (as set forth in section 3(f) above).

Similar to that shown in FIGS. 3 and 4, the embodiment in FIG. 5 includes the U-shaped part (46a) having an inner U-shaped surface (46a') and an outer U-shaped surface (46a") configured between two raised flange portions (46c), as labelled in FIG. 5B. Each raised flange portions (46c) has a respective raised flange portion surfaces (46c'), as labelled in FIG. 5B. The inner U-shaped surface (46a') rests on an outer sample tube surface (45a) of the sample tube (45). The two raised flange portions (46c) rest on and are supported by the sample support rails (41), e.g., consistent with that shown in FIG. 5.

Note that in the embodiments shown in FIGS. 3, 4 and 5 the thermal assemblies are beneath the sample support rails (1, 11, 21, 31, 41) and are therefore may be more prone to sample contamination.

Sample Support Rails (1, 11, 21, 31, 41),

The sample support rails (1, 11, 21, 31, 41) show in FIGS. 1-5 are configured to extend as parallel sample support rails. Moreover, the sample support rails (1, 11, 21, 31, 41) are shaped like circular cylindrical rods, each extending along a parallel axis. By way example, the embodiment shown herein have one or more curved surfaces of the sample tube adaptor (6, 16, 26, 36, 46) physically resting on and supported by corresponding curved surfaces of the sample support rails (1, 11, 21, 31, 41).

FIG. 6

FIG. 6 shows the overall equipment (100) having the polarimeter (7) arranged in relation to the frame-like structure or instrument chassis (102) and a light source (120) for performing the sample analysis, e.g., consistent with that described below. In FIG. 6, only the basic components of the polarimeter (7) are labelled to reduce clutter in the Figure, e.g., including where the basic components are the sample support rails (1), the temperature controlled plate (2), the Peltier Devices (3), the heatsink (4), the sample tube (5), the sample tube adaptor (6) and a detector/analyzer (8) for performing the sample analysis. See that described in relation to FIG. 1 for a more detailed description thereof. In FIG. 6, the frame-like structure or instrument chassis (102) is coupled on the bottom to the sample support rails (1) and is coupled on the top to the thermal assembly, e.g., which may include the Peltier Devices (3), the heatsink (4), the sample tube (5), as shown.

By way of example, and consistent with that shown in FIG. 6, one or more frame members like elements (104, 106) may be coupled to one sample support rail (1), and one or more frame members like element (105) may be coupled to the other sample support rail (1). In order to reduce clutter, only one frame member is shown coupled to the other sample support rail (1). However, the scope of the invention is not intended to be limited to the type, kind or structural arrangement between the frame-like structure or instrument chassis (102) and the sample support rails (1). Embodiments are envisioned, and the scope of the invention is intended to include, other types, kinds or structural arrangements between the frame-like structure or instrument chassis (102) and the sample support rails (1) that are now known or later developed in the future.

By way of example, and consistent with that shown in FIG. 6, one or more frame members like elements (108, 110) may be coupled to one or more of the components (2), (3) and (4) on each side of the thermal assembly. However, the scope of the invention is not intended to be limited to the type, kind or structural arrangement between the frame-like structure or instrument chassis (102) and the thermal assembly. Embodiments are envisioned, and the scope of the invention is intended to include, other types, kinds or structural arrangements between the frame-like structure or instrument chassis (102) and the thermal assembly that are now known or later developed in the future. For example, the one or more frame members like elements (108, 110) may be coupled to one component like element (2) on each side of the thermal assembly.

By way of example, and consistent with that shown in FIG. 6, one or more frame members like element (112) may be coupled to the light source (120). However, the scope of the invention is not intended to be limited to the type, kind or structural arrangement between the frame-like structure or instrument chassis (102) and the light source (120). Moreover, the light source (120) may take the form of a laser for providing laser light L to the sample tube (5), e.g., consistent with that shown in FIG. 6. Moreover, the scope of the invention is intended to include, and embodiments are envisioned in which, using an incandescent lamp or an LED. In effect, the scope of the invention is not intended to be limited to the type or kind of light source used, and may include other types or kinds of light sources either now known or later developed in the future.

Based upon the aforementioned structural understanding between the frame-like structure or instrument chassis (102), the sample support rails (1) and the thermal assembly (2), (3) and (4), in operation the sample tube adaptor (6) having the sample tube (5) may be removably arranged or placed between the sample support rails (1) and the thermal assembly (2), (3) and (4) for performing the sample analysis. When the sample tube adaptor (6) having the sample tube (5) rests on, and is physically supported by, the sample support rails (1), there is registration between the sample tube (5) and the light (L) from the light source (120), and there is also a thermal path for heat transfer between the thermal assembly (2), (3) and (4) and the sample tube (5) via the sample tube adaptor (6), e.g., so as to provide the aforementioned three key elements (see subparagraphs 1(*a*), (*b*) and (*c*) set forth above) for the sample analysis. As a person skilled in the art would appreciate, the sample analysis may include heating the sample contained in the sample tube (5) using the thermal assembly (2), (3) and (4), and/or interrogating the sample contained in the sample tube (5) using the light source (120). The scope of the invention is not intended to be limited to the type or kind of sample analysis performed. Embodiments are envisioned, and the scope of the invention is intended to include, many different types or kinds of sample analysis technique that are now known or later developed in the future.

As a person skilled in the art would appreciate, the overall equipment (100) shown in FIG. 6 may also include other types or kind of components not shown or described, e.g., since they do not form part of the underlying invention disclosed herein. By way of example, such other types or kind of components may include one or more controller for the thermal assembly or the light source, etc.

Detectors/analyzers are known in the art, and the scope of the invention is not intended to be limited to any particular type or kind thereof either now known or later developed in the future.

The Scope of the Invention

It should be understood that, unless stated otherwise herein, any of the features, characteristics, alternatives or modifications described regarding a particular embodiment herein may also be applied, used, or incorporated with any other embodiment described herein. Also, the drawing herein is not drawn to scale.

Although the present invention is described by way of example in relation to a centrifugal pump, the scope of the invention is intended to include using the same in relation to other types or kinds of pumps either now known or later developed in the future.

Although the invention has been described and illustrated with respect to exemplary embodiments thereof, the foregoing and various other additions and omissions may be made therein and thereto without departing from the spirit and scope of the present invention.

I claim:

1. Apparatus configured to perform a sample analysis of a sample contained in a sample tube, comprising:
    a combination of a sample tube adapter and sample support rails;
    the sample tube adapter being made of conductive material, and configured with a first part to at least partially contain and touch a sample tube having a sample therein, and configured with a second part to provide a thermal path for heat transfer to and from the sample tube and a thermal assembly for performing a sample analysis; and
    the sample support rails configured to
        receive the sample tube adapter to provide physical support for the sample tube for performing the sample analysis,
        orient the sample tube adapter in relation to the thermal assembly so there is contact between the second part of the sample tube adapter and some part of the thermal assembly in order to provide the thermal path for heat transfer to and from the sample tube and the thermal assembly for performing the sample analysis, and
        align the sample tube adapter in relation to a light source so there is a registration between the sample tube and a light beam provided by the light source for performing the sample analysis.

2. Apparatus according to claim 1, wherein the first part of the sample tube adaptor has an inner curved surface to rest on, and make contact with, an outer curved surface of the sample tube having the sample therein.

3. Apparatus according to claim 1, wherein the second part of the sample tube adaptor has a flat surface to make contact with a temperature control plate of the thermal assembly.

4. Apparatus according to claim 1, wherein the sample tube adaptor has two end raised flange portions configured to rest on, and be supported by, the sample support rails.

5. Apparatus according to claim 2, wherein the inner curved surface is U-shaped.

6. Apparatus according to claim 1, wherein the sample support rails are configured to extend in parallel with one another.

7. Apparatus according to claim 1, wherein the sample tube adaptor has a curved exterior surface configured to rest on, and make contact with, an outer curved surface of the sample tube having the sample therein.

8. Apparatus according to claim 1, wherein the second part of the sample tube adaptor comprises two blades extending downwardly that straddle a vertical blade extending upwardly of a temperature control plate of the thermal assembly to provide the thermal path for heat transfer to and from the sample tube and the thermal assembly for performing the sample analysis.

9. Apparatus according to claim 1, wherein the second part of the sample tube adaptor comprises a blade extending downwardly having a blade surface that abuts against a temperature control plate of the thermal assembly to provide the thermal path for heat transfer to and from the sample tube and the thermal assembly for performing the sample analysis.

10. Apparatus according to claim 1, wherein the second part of the sample tube adaptor comprises two blades extending downwardly, each blade having a corresponding blade surface that respectively abuts against a corresponding temperature control plate of the thermal assembly to provide the thermal path for heat transfer to and from the sample tube and the thermal assembly for performing the sample analysis.

11. Apparatus according to claim 1, wherein the apparatus comprises the thermal assembly having a combination of a temperature control plate, a Peltier device and a heatsink.

12. Apparatus according to claim 1, wherein the apparatus comprises the light source for providing the light beam.

13. Apparatus according to claim 1, wherein the light beam is a laser light beam, or an incandescent light beam, or an LED light beam.

14. Apparatus according to claim 1, wherein the apparatus comprises the thermal assembly and the light source; and also comprises an instrument chassis configured to mount the sample support rails in relation to the thermal assembly and the light source, so that when the sample support rails receive the sample tube adapter, the sample support rails orient the sample tube adapter in relation to the thermal assembly so there is contact between the second part of the sample tube adapter and the part of the thermal assembly in order to provide the thermal path for heat transfer to and from the sample tube and the thermal assembly for performing the sample analysis, and align the sample tube adapter in relation to the light source so there is a registration between the sample tube and a light beam provided by the light source for performing the sample analysis.

15. Apparatus according to claim 1, wherein the apparatus comprises a detector/analyzer configured to receive the light beam passing through the sample tube and perform the sample analysis.

* * * * *